United States Patent [19]

Holman

[11] Patent Number: 4,915,113
[45] Date of Patent: Apr. 10, 1990

[54] METHOD AND APPARATUS FOR MONITORING THE PATENCY OF VASCULAR GRAFTS

[75] Inventor: Daniel G. Holman, Phoenix, Ariz.
[73] Assignee: Bio-Vascular, Inc., St. Paul, Minn.
[21] Appl. No.: 285,529
[22] Filed: Dec. 16, 1988
[51] Int. Cl.$^4$ ............................................. A61B 5/02
[52] U.S. Cl. ................................. 128/691; 128/662.04
[58] Field of Search ................. 128/661.08–661.10, 128/662.05–662.06, 691, 692; 73/644

[56] References Cited

U.S. PATENT DOCUMENTS

| | | | |
|---|---|---|---|
| 3,568,661 | 3/1971 | Franklin | 128/661.08 |
| 3,661,146 | 5/1972 | Peronneau et al. | 128/662.04 |
| 4,270,549 | 6/1981 | Heilman | 128/784 |
| 4,355,643 | 10/1982 | Laughlin et al. | 128/662.04 |
| 4,823,800 | 4/1989 | Compos | 128/661.08 |

Primary Examiner—Francis Jaworski
Attorney, Agent, or Firm—Haugen and Nikolai

[57] ABSTRACT

An implanted flow meter device for monitoring blood flow through a vascular graft is described. At the time that the vascular graft is implanted, a ring-like clip having Doppler crystal transducers mounted thereon is made to surround the graft with the acoustic axis of the transducers being generally longitudinally and internally directed relative to the graft. At the same time, an electrical plug-type connector is subcutaneously implanted at a desirable access site and electrical conductors connect terminals on that plug to the Doppler crystal transducers. When a blood flow reading is desired, a small incision can be made at the implant site to provide access to the plug-type connector, allowing a Doppler transmitter/receiver to be connected to that transducers via the plug connection.

15 Claims, 2 Drawing Sheets

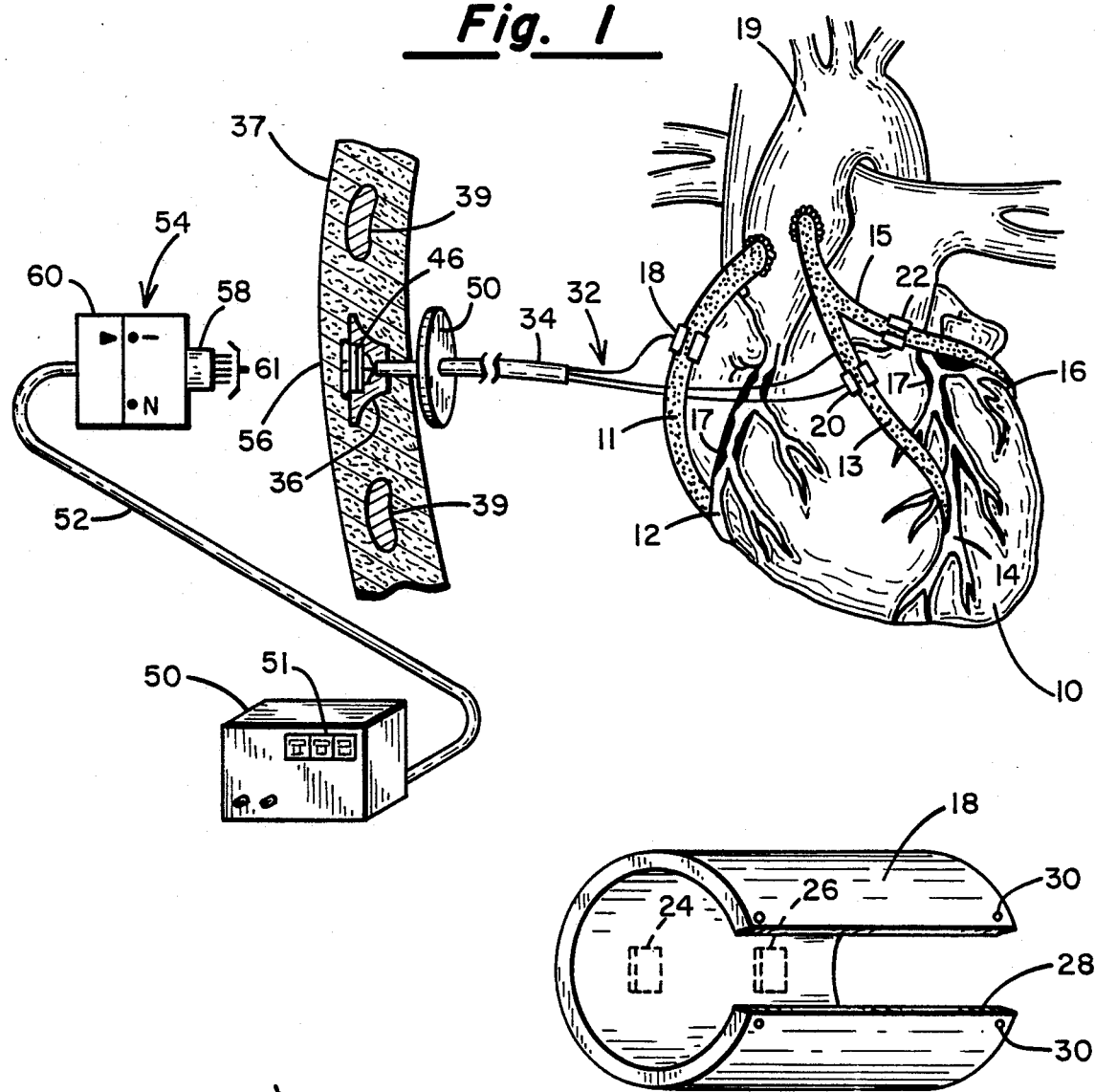
Fig. 1
Fig. 2
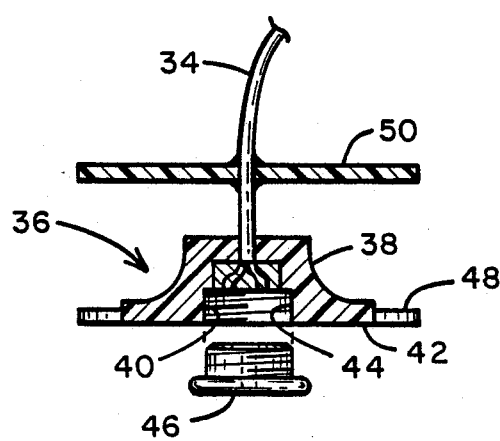
Fig. 3

METHOD AND APPARATUS FOR MONITORING THE PATENCY OF VASCULAR GRAFTS

BACKGROUND OF THE INVENTION

I. Field of the Invention:

This invention relates generally to medical apparatus for monitoring blood flow in a blood vessel, and more particularly to an implantable Doppler flow meter for measuring the blood flow through an implanted vascular graft so that its patency can be periodically measured.

II. Discussion of the Prior Art:

In treating coronary artery disease, it is sometimes necessary to bypass one, two, three or four coronary arteries with an autologous graft, usually harvested from the patient's saphenous vein in the thigh or leg. The bypass graft is sutured or otherwise joined to the heart to act as a shunt around a blocked or partially blocked coronary artery.

It is important that the condition of the graft be monitored, post-surgery, to detect the further build-up of stenotic lesions or other obstructions to the flow of blood through that implanted graft. Various catheterization procedures are known for assessing the flow characteristics of a blood vessel or blood vessel graft. For example, using a thermal dilution technique, a catheter having two or more spaced-apart temperature sensitive elements thereon is routed through the vascular system to the site where the measurements are to be taken. Subsequently, a bolus injection of cold saline solution is introduced into the blood stream proximally of the measuring elements and then a measurement is taken of the time required for that cold liquid, driven by the blood, to pass between the spaced-apart temperature sensors. Knowing this time interval and other characteristics of the catheter, flow rates through the site can be measured and the condition of the vessel or graft inferred.

Another catheterization procedure involves the use of so-called impedance plethysmography. Here, a catheter having spaced-apart drive electrodes on either side of a pair of sense electrodes near the distal end portion thereof is routed through the vascular system to the site to be observed. A relatively high frequency alternating current signal is applied across two spaced-apart outer drive electrodes and the resulting signal developed across the pair of intermediate sensing electrodes is detected. The pulsating flow of blood through the site in question causes the sensed signal to be modulated and this modulating envelope signal corresponds to impedance swings which can be shown to be directly related to the volume of the blood vessel or graft being monitored.

It is also known in the art that piezoelectric transducers can be disposed on the distal end of a catheter and routed to a site of interest. One of the transducers is then driven by a signal generator located at the proximal end of the catheter to create an acoustic wave. Echo signals reflected back from blood cells to the pickup transducer creates an electrical signal which is fed to the receiver. Knowing the frequency of the acoustic energy and certain other parameters, the Doppler frequency shift can be detected to provide an indication of the rate of flow of blood through the site in question.

Further information concerning Doppler flow catheters can be gained from reading the following U.S. patents: Johnston U.S. Pat. Nos. 4,674,336; Johnston 4,637,401; Millar 4,665,925; and Abrams et al 4,671,295. The foregoing patents also contain references to still other patents and publications wherein Doppler catheters are used to measure blood velocity and flow rate in diseased arteries.

The introduction of catheters into the vascular system is not an altogether risk-free procedure. There are instances where the introduction of an angiographic catheter has damaged the endothelial lining of the blood vessel creating a flap which can block the vessel creating ischemia. Should this happen, it is again necessary to surgically repair the blood vessel and, in the case of coronary bypass surgery, would again require the patient's chest to be opened. Even if the blood vessels themselves are not damaged by the introduction of the catheter, there is always a chance that a particle of plaque may be dislodged from the interior walls of the blood vessel and may float to a point where a stroke or other life-threatening episode can occur due to a blockage in a small blood vessel.

Because of the above-described types of concerns, it has been difficult to obtain patient compliance with the need to periodically monitor the vascular graft over a period of time following its original implant.

It is accordingly a principal object of the present invention to provide an improved method and apparatus for monitoring the flow characteristics of an implanted blood vessel graft.

Another object of the invention is to provide an implantable system for monitoring blood flow through surgically implanted grafts which is substantially benigned.

Yet another object of the invention is to provide an implantable Doppler flow meter system which can readily be accessed on a routine basis to determine the state of the implanted grafts.

SUMMARY OF THE INVENTION

In accordance with the present invention, at the time that the original surgery is performed to install one or more vascular grafts, a ring-like clip is made to surround the graft itself and mounted on the clip are a pair of Doppler crystal transducers which are oriented so as to define an acoustic axis penetrating the vessel walls and extending generally longitudinally within the lumen of the graft. Electrical conductors are used to connect the Doppler crystal transducers to a plug-type connector which is implanted subcutaneously at a location just below the skin surface and easy to locate by touch.

At a time of prescribed follow-up, the surgeon may make a small incision through the skin to gain access to the implanted plug. A Doppler transmitter/receiver module may then have its output/input terminals connected by a plug to the plug that had earlier been implanted. Thus, appropriate drive signals can be applied to the Doppler crystal transducer on the ring clip with the resulting echo signal picked up by a second transducer converted to an electrical signal in the receiver. The Doppler module is arranged to determine the frequency shift between the transmitted and received signals. This frequency shift is then proportional to the flow rate of blood through the graft.

It is also found convenient and advisable to provide an infection barrier in the form of a Dacron patch or collar through which the electrical conductors pass in going from the transducer crystals to the implanted plug. Any germs entering the incision are effectively blocked from reaching the site of the grafts.

It is also envisioned that telemetry techniques can be used to avoid the necessity of puncturing the skin to gain access to the implanted plug. More particularly, signals may be electro-magnetically transmitted through the skin to an implanted transmitter/receiver in much the same way that external programmers are now used to read out information from implanted cardiac pacemakers and to alter the operating parameters of such pacemakers.

The foregoing features and advantages of the invention will become apparent to those skilled in the art from the following detailed description of a preferred embodiment, especially when considered in conjunction of the accompanying drawings in which like numerals in the several views refer to corresponding parts.

DESCRIPTION OF THE DRAWINGS

FIG. 1 is a view of a human heart following coronary bypass surgery and with the implanted Doppler flow meter apparatus of the present invention installed;

FIG. 2 is an enlarged view of a Doppler crystal transducer clip ring in accordance with the invention; and FIG. 3 is an enlarged view of the subcutaneous plug connector employed in the apparatus of FIG. 1.

DESCRIPTION OF THE PREFERRED EMBODIMENT

Figure 4:
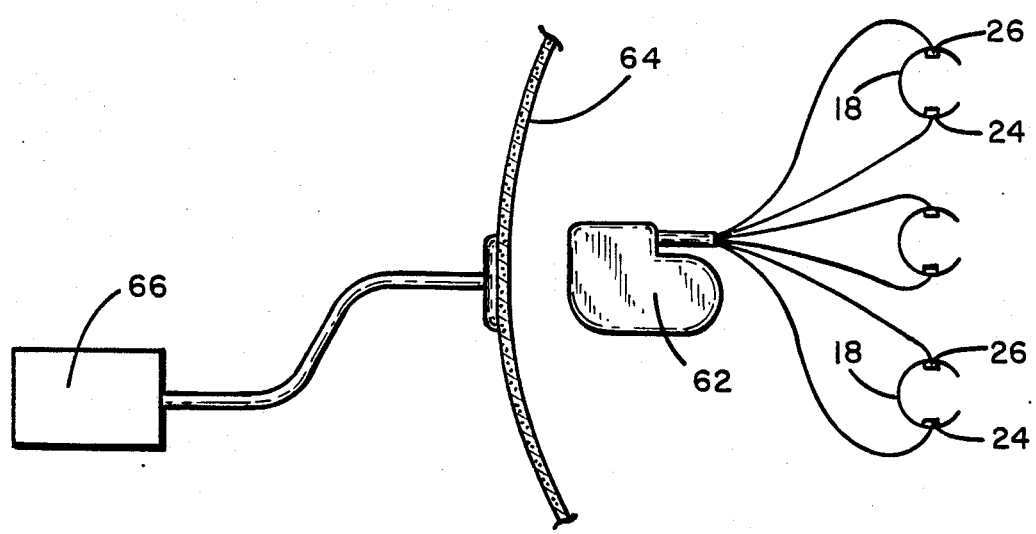
FIG. 4 illustrates an arrangement for telemetric transmission of blood flow information transcutaneously.

Referring first to FIG. 1, the invention will be described in connection with its use for monitoring blood flow through coronary bypass grafts, it being understood that those skilled in the art will be able to apply the invention to other blood vessels and vascular grafts as well. The heart is identified by numeral 10 and also illustrated are the right coronary artery 12, the anterior interventricular branch of the left coronary artery 14 and the circumflex branch of the left coronary artery 16. These arteries are depicted as being diseased in that they contain a build-up of plaque and tissue deposits 17 which tend to limit the natural flow of blood to the heart muscle. Also illustrated in FIG. 1 are three bypass grafts 11, 13 and 15 Which are surgically joined to the ascending aorta 19 at their proximal end and which bridge the stenotic lesions 17 before being joined to the distal portions of the affected coronary arteries 12,14 and 16.

In accordance with the present invention, at the time of the bypass surgery, transducer mounting rings 18, 20 and 22 are put in place surrounding the grafts 11, 13 and 15 so as to intimately position the Doppler crystal transducer elements 24 and 26 (FIG. 2) against the outer periphery of the grafts.

FIG. 2 shows a substantially enlarged view of the transducer mounting ring clip 18, it being typical of the others employed. The ring is fabricated from a non-fibrosing, body compatible material such as titanium, stainless steel or any one of a number of medical-grade plastics now available as being suitable for implantation within the body. The clip is seen to be generally annular in its construction except it is split longitudinally as at 28. With no limitation intended, the split ring clip may have an outside diameter of 1.2 centimeters and may be approximately 8 millimeters in length. The slot or gap may typically measure approximately 3 millimeters. The wall thickness of the clip varies smoothly from a minimum of approximately 1 millimeter proximate the slit or gap 28 and a maximum of about 3 millimeters along its back surface opposite the gap 28. Small holes 30 are located immediately adjacent the split for allowing sutures to be used, if necessary, to suture the clip to the surrounding tissue and thereby more firmly attach the ring to the vascular graft segment with which it is used.

The Doppler crystal sending transducer 24 and the receiving transducer 26 are internally embedded within the wall of the ring and are physically oriented so that the acoustic wave produced by the transmitting crystal 24 will be internal of the graft and directed somewhat longitudinally therealong. Likewise, the receiving Doppler crystal 26 is also oriented so as to receive acoustic energy reflected from the moving blood cells as they pass through the vascular graft.

The Doppler transducers 24 and 26 preferably comprises piezoelectric ceramic, such as lead-zirconate-titinate material, which is about 0.002 to 0.005 inch in thickness and of an area approximately in the range of from 0.02 to 0.05 square inches. It may typically be designed to resonate at a frequency of 15 to 30 megahertz when driven by an appropriate high frequency oscillator. The transmitting crystal produces an acoustic signal at the specified resonant frequency. The receiving Doppler crystal transducer 26 is appropriately matched to the transmitting crystal so that when it receives the reflected acoustic energy, it converts the energy into an electrical signal whose frequency is shifted slightly from that of the driving oscillator. The frequency shift, $\Delta f$, can be expressed by the formula:

$$\Delta f = 2F(V/c)\cos\phi$$

where F is the transmitted frequency; V is the blood velocity; c is the velocity of sound in blood; and $\phi$ is the angle between the fluid flow axis and the acoustic axis of the Doppler crystals. In that the transducers 24 and 26 are stationary, the angle $\phi$ remains constant, as does the transmitted frequency, F, and the velocity of sound in blood. Hence, the frequency shift is directly and linearly proportional to the velocity of the blood flowing through the graft.

Referring again to FIG. 1, the transmitting crystals 24 and the receiving crystals 26 for each of the clips 18, 20 and 22 are connected by silicone insulated electrical conductors indicated generally by numeral 32 and routed through a silicone rubber sheath 34 to an implanted plug 36. The plug 36 is disposed beneath the skin 38 at a suitable access site. In the case of the Doppler flow meter implant for use with coronary bypass surgery, it has been found convenient to locate the plug 36 intercostally between adjacent ribs 40, the plug being suitably anchored in place so that it cannot drift.

Referring next to FIG. 3, there is shown a greatly enlarged cross-sectional view of the plug 36. It is seen to comprise a molded silicone body 38 having a circular bore 40 extending inwardly from a generally flat top surface 42. The bore 40 is lined with a stainless steel ring 44 which is threaded to receive a mating stainless steel cap 46 which is also coated with silicone rubber. When the cap 46 is screwed in place, it provides a fluid-tight seal, preventing the ingress of body fluids and/or tissue growth. Also contained within the molded body 38 are a set of electrical contacts 46 which are joined to the proximal ends of the conductors 32. A silicone or Dacron suture ring 48 provides a means whereby the plug 36 can be fixedly anchored in position beneath the skin.

There is further shown in FIG. 1 a Dacron collar 50 through which the sheath 34 and the conductors 32 pass in going to the plug 36. This patch serves as an infection barrier for preventing any organisms which may be introduced during the monitoring stage from traversing the lead assembly 34 to the heart tissue or other internal organs disposed within the chest cavity.

The Doppler electronic transmitter/receiver module is identified by numeral 50 and is coupled by a cable 52 to an electro-mechanical plug assembly 54. When a blood flow measurement is to be taken, the physician makes a small incision in the skin at the point identified by numeral 56 and then proceeds to remove the cap member 46 from the plug housing. The end 58 of the plug 54 may then be inserted into the bore 40 and, in doing so, the electrical contacts 61 of the plug 58 will mate with the corresponding contacts in the implanted plug 36. By rotating the cap portion 60 of the assembly 54 about a centerpost (not shown), appropriate electrical connections can be made between the electronics module 50 and the transducers 24 and 26 on a selected one of the rings 18, 20 or 22 so as to drive the transmitting crystal and to pick up the resulting voltage induced in the receiving crystal. The received signals are fed back to the module 50 for processing ultimate readout of the velocity on the display panel 51. Knowing the dimensions of the graft in question at the time of implant, any change in velocity over time can be related to increases in the build-up of deposits on the interior walls of the graft.

As indicated earlier and with reference to FIG. 4, it is also possible to implant the driving oscillator for the transducers and the circuitry for detecting the frequency shift in a body compatible enclosure 62. The energy necessary to drive the sending transducer 24 can be electro-magnetically coupled through the skin 64 to the implanted electronic module 62. Moreover, the information read back from the receiving transducers 26 can likewise be telemetered from enclosure 62 through the skin to an external monitor 66 using known techniques.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. Implantable flow meter apparatus for monitoring vascular graft patency comprising:
   (a) at least one ring member for surrounding a blood vessel graft intermediate its ends, said at least one ring member supporting transducer means thereon to define an axis extending internal of said blood vessel graft when said at least one ring member is installed on said blood vessel graft;
   (b) implantable electrical means positionable subcutaneously at a predetermined access site displaced from said one at least one ring member;
   (c) conductor means coupling said transducer means to said electrical means; and
   (d) barrier patch means having an area much greater than the cross-sectional area of said conductor means, said conductor means passing generally through the center of said patch means for inhibiting passage of infection producing organisms from said access site along said conductor means.

2. The implantable flow meter apparatus as in claim 1 wherein said transducer means comprises Doppler crystal transducer means.

3. The implantable flow meter apparatus as in claim 2 wherein said electrical means comprises an implantable electrical connector having a plurality of electrical contacts, said contacts being coupled by conductor means to said Doppler crystal transducer means.

4. The implantable flow meter apparatus as in claim 3 and further including:
   (a) signal transmitting/receiving means disposed outside the body and having connector means joinable to said implantable connector means through an incision made at said access site.

5. The implantable flow member as in claim 1 wherein said barrier patch means comprises a Dacron patch; and a silicon rubber seal covering the intersection of said conductor means with said patch means.

6. The implantable flow meter as in claim 2 and further including a signal transmitter/receiver for implantation within the body of a patient and including terminal means joined to said implantable connector means; and means for electromagnetically telemetering information from said signal transmitter/receiver transcutaneously to monitoring means external to the body.

7. The implantable flow meter as in claim 2 wherein said at least one ring member is longitudinally split and said Doppler crystal transducer means includes first and second transducer elements supported by said at least one ring member, said transmitting/receiving means being electrically joinable to the first of said transducer elements in driving relation and to the second of said transducer elements in receiving relation.

8. Implantable Doppler flow meter apparatus for monitoring potency of coronary artery bypass grafts post surgery, comprising:
   (a) a plurality of ring members equal in numbers to the number of grafts to be placed on the heart for individually surrounding said grafts intermediate their ends, each of said ring members supporting Doppler crystal transducing means thereon to define an acoustic axis extending generally longitudinally and internally of the artery bypass graft with which it becomes associated;
   (b) an implantable connector means having a plurality of contacts, said connector means being positionable subcutaneously at a predetermined access site remote from said ring members;
   (c) conductor means coupling said Doppler crystal transducing means to said contacts of said connector means; and
   (d) infection barrier patch means having an area much greater than the cross-sectional area of said conductor means, said conductor means passing generally centrally through said patch means at a point between said connector means and said transducing means for preventing infection producing organisms from migrating along said conductor means to the site of said ring members.

9. The implantable Doppler flow meter apparatus as in claim 8 and further including:

(a) signal transmitting/receiving means disposed outside the body and having an electrical connector complementary to and connectable with said implantable connector means through an incision made at said access site; and
(b) switching means for coupling said transmitting/receiving means to selected ones of said plurality of contacts.

10. The implantable Doppler flow meter apparatus as in claim 8 wherein each of said plurality of ring members is split to allow it to be fitted onto an arterial bypass graft after said graft is sutured in placed on the heart.

11. The implantable Doppler flow meter apparatus as in claim 10 wherein said Doppler crystal transducing means includes first and second piezoelectric crystals embedded in said ring members.

12. The implantable Doppler flow meter as in claim 11 and further including:
(a) signal transmitting/receiving means having output means and input means and disposed outside the body;
(b) an electrical connector polarized to mate with said plurality of contacts of said implantable connector through an incision made at said access site and connected to the respective output from and input to said transmitting/receiving means; and
(c) switching means for selectively coupling said output from and input to said transmitting/receiving means to said first and second piezoelectric crystals on any one of said plurality of ring member.

13. The Doppler flow meter as in claim 12 wherein said switching means is integral with said electrical connector.

14. The implantable flow meter apparatus as in claim 8 wherein said implantable connector includes a removable plug for blocking entry of tissue and body fluids into said implantable connector.

15. The implantable Doppler flow meter as in claim 8 wherein said infection barrier patch means comprises a generally flat flexible Dacron collar surrounding said conductor means distally of said implantable connector means and proximally of said ring members.

* * * * *

UNITED STATES PATENT AND TRADEMARK OFFICE
CERTIFICATE OF CORRECTION

PATENT NO. : 4,915,113

DATED : April 10, 1990

INVENTOR(S) : Daniel G. Holman

It is certified that error appears in the above-identified patent and that said Letters Patent is hereby corrected as shown below:

Column 6, line 42, change "potency" to -- patency --.

Column 7, line 12, change "placed" to -- place --.

Signed and Sealed this

Eleventh Day of June, 1991

Attest:

HARRY F. MANBECK, JR.

Attesting Officer

Commissioner of Patents and Trademarks